United States Patent [19]

Hofeldt

[11] Patent Number: 5,099,858
[45] Date of Patent: Mar. 31, 1992

[54] DEVICE FOR MEASURING THE PULFRICH STEREO-ILLUSION PHENOMENON AND FOR DETECTING OCULAR AND OPTIC NERVE DISEASE

[76] Inventor: Albert J. Hofeldt, 116 E. 66th St., New York, N.Y. 10021

[21] Appl. No.: 583,224

[22] Filed: Sep. 14, 1990

[51] Int. Cl.$^5$ ............................................. A61B 13/00
[52] U.S. Cl. ..................................... 128/745; 600/27; 351/201
[58] Field of Search ........................ 128/745; 600/27; 351/201, 244

[56] References Cited

U.S. PATENT DOCUMENTS

| | | |
|---|---|---|
| 1,545,652 | 7/1925 | Hagerty . |
| 2,362,588 | 11/1944 | Shepard ................ 351/201 |
| 2,590,101 | 3/1952 | Henschke et al. . |
| 2,781,042 | 2/1957 | Bartow . |
| 3,623,799 | 11/1971 | Millodot . |
| 4,131,342 | 12/1978 | Dudley .................... 352/43 |
| 4,564,274 | 1/1986 | Clark ...................... 351/233 |

FOREIGN PATENT DOCUMENTS 0271410  6/1988  European Pat. Off. .

OTHER PUBLICATIONS

Hofeldt—Clinical Applications of the Pulfrich Phenomenon, Ocular Inflammation Ther. 1:117-123, Jun. 1983.

Tredici et al.—The Pulfrich Effect in Ansiometropic Amblyopia and Strabismus, American Journal of Ophthalmology, 98:499-503, Oct. 1984.

Hofeldt et al.—Pulfrich Stereo-Illusion Phenomenon in Serous Sensory Retinal Detachment of the Macula, American Journal of Ophthalmology 100:576-580, Oct. 1985.

Primary Examiner—Max Hindenburg
Attorney, Agent, or Firm—Rosenman & Colin

[57] ABSTRACT

A device useful in diagnosing ocular and optic nerve diseases in people who are capable of experiencing the Pulfrich stereo-illusion phenomenon which comprises an enclosure having two eye pieces, a bob and a reference point for the bob within said bob is positioned below the top of the reference point but slightly in front of it when the patient to be tested is standing in front of the device, illumination means in front of the bob and reference point, reflective means for viewing the bob and reference point through the eye pieces, means for varying the amount of light perceived through the eye pieces by each of the eyes individually of the patient to be tested, means for varying the amount of illumination and means for causing the bob to arc in a pendulum movement in front of the reference point.

24 Claims, 4 Drawing Sheets

DEVICE FOR MEASURING THE PULFRICH STEREO-ILLUSION PHENOMENON AND FOR DETECTING OCULAR AND OPTIC NERVE DISEASE

The present invention resides in a device which enables ocular and optic nerve diseases to be easily and reliably detected.

The Pulfrich stereo-illusion is a psychophysical response dependent on stereoscopic binocular central vision. The Pulfrich stereo-illusion phenomenon of a frontal plane oscillating object appearing to travel in an elliptical orbit when viewed with unequal binocular illumination was described in 1922 by Carl Von Pulfrich, a German scientist. Viewed from above, the direction of the orbit is clockwise when the image perceived by the left eye is dimmer and counter-clockwise when the image perceived by the right eye is dimmer. The apparent depth of the orbit has been found to vary directly with the velocity of the oscillating pendulum, the difference in the binocular retinal illumination, and the distance from the observer to the pendulum bob, and inversely with the background illumination level.

Pulfrich postulated that the stereo effect resulted from a prolonged latent period of vision along the afferent pathway of the eye perceiving the dimmer image. Subsequent investigators using the episcotistor, random dot stereo-movies, and visual-evoked responses, have confirmed that the latent period of vision increases as the retinal illumination decreases. The synchronous conduction of impulses originating from corresponding retinal points produces disparity in the simultaneous perception of these stereo-pairs and hence the false sensation of depth to the viewer.

The minimum visual and stereoscopic acuities required to appreciate the normal stereo-illusion were first described by me in "Clinical Applications of the Pulfrich Phenomenon" in Ocular Inflammation Ther. 1:117-123 (1983) and in my EPA 87402784.0 published June, 15, 1988.

It has been suggested in the literature that the appreciation of the Pulfrich stereo-illusion depends not only on normal vision, but also upon the skill of the individual as an observer. Consequently, the inability to induce the normal stereo-illusion by placing a filter before one eye has not been considered a sign of disease since factors other than visual acuity and stereopsis have been thought to influence the appreciation of the stereo-illusion. However, using my device, I have shown that all normal sighted persons are able to see the stereo-illusion and in fact it is not possible to suppress the stereo-illusion for normal sighted persons under the testing conditions.

Utilizing the pulfrich stereo-illusion, I have developed a device I call the stereo-photometer for determining the presence of diseases affecting the visual system which interferes with central scuity, stereopsis, or the brightness equality of the images perceived by the right and left visual pathways. Reduced perceived brightness can be the result of pre-retinal, retinal, or optic nerve disease. Regardless of the anatomical site responsible for the brightness imbalance of the right and left visual pathways, the correct neutral density filter positioned before the eye perceiving the brighter image will bring the right and left visual pathways into balance. In the development of the stereo-photometer, I have applied the Pulfrich stereo-illusion principle as a sensitive brightness balance to compare and measure the visual input to the right and left visual pathways. The stereo-photometer is designed to precisely control and measure the luminance to each eye with variable neutral density filters while maintaining constant all other variables known to affect the stereo-illusion. The luminance difference between the two eyes (interocular) can be calculated from the measured luminance to each eye.

The stereo-illusion is a normal phenomenon only when occurring within a certain range of interocular luminance differences. A disease of the visual system is present when: (1) the stereo-illusion is seen by the subject without attenuating the luminance to either eye (spontaneous response), (2) the luminance attenuation to induce the stereo-illusion is different for each eye and outside the normal range (asymmetric induced response), (3) the luminance attenuation to neutralize an induced stereo-illusion created with a standard value neutral density filter is different for each eye and outside the normal range (asymmetric neutralization response), (4) a subthreshold neutral density filter placed before one but not the other eye induces the stereo-illusion, or, (5) the stereo-illusion cannot be induced at any interocular luminance difference (non-inducible response).

The spontaneous response has a specific orientation which dictates the pathway perceiving the dimmer image, i.e., clockwise for the left pathway and counter-clockwise for the right pathway. Testing with the stereo-photometer, the spontaneous response can be precisely quantitated by balancing the brightness disparity between the right and left visual pathways with the progressive neutral density filter before the eye perceiving the brighter image until the endpoint is reached. The endpoint is the moment the pendulum bob motion changes from rotational about a reference point to planar.

The spontaneous response is seen by the person without altering the ambient viewing conditions and occurs when the brightness disparity between the right and left visual pathways exceed a threshold difference. This happens in pre-retinal diseases causing unequal pupils or media opacities, retinal diseases causing neuronal dysfunction within the retina, or optic nerve disease causing delay nerve conduction velocity as I reported in "Clinical Application of the Pulfrich Phenomenon", Ocular Inflammation Ther. 1:117-123 (1983) and "Pulfrich Stereo-illusion Phenomenon in Serous Sensory Retinal Detachment of the Macula", Amer. J. Ophthalmol. 100:576-580 (1985) and in my EPA 87402784.0, published June 15, 1988.

Disease conditions exist in which the brightness appreciation is less in one visual pathway than the other but not to the degree that produces the spontaneous response. This subthreshold brightness disparity can be detected by the induction or neutralization technique. If the brightness appreciation is unequal for the two sides, the induction or neutralization endpoints will be different for each side and the larger the interocular difference the more the brightness disparity. An alternative induction technique to detect a subthreshold brightness defect is to use a neutral density filter of less density than required to induce the stereo-illusion in normal sighted people. Placing this sub-threshold filter before the eye with the subthreshold defect the combination will result in an interocular difference of the threshold level for the stereo-illusion. When this same subthreshold filter is placed before the opposite eye, threshold level can not be reached since that eye must be functioning at a high relative brightness level and would require a filter of higher density than required to induce the stereo-illusion in a normal sighted person.

The design of the pendulum bob and the reference point is important in maximizing the stereo-illusion effect for the observer. A fixation target positioned at the center of the pendulum movement gives a reference point for the position of the bob in space and to the location of the pathway of the illusionary orbit. The fixation target is best positioned behind the bob so that the bob does not disappear each time it transverses the fixation target.

I have discovered that an erect cone is a particularly useful fixation target and an inverted conical shape for the pendulum bob best fulfills the shape requirements to achieve the optimum desired combination of large bob and fixation target size, maximum bob and fixation target overlapping distances, and minimum bob and fixation target overlapping areas. The area of overlap should be large enough to allow the observer to position the proximity of the bob in space but small enough not to distract from the stereo-illusion by the visual clue that the bob does not disappear behind the fixation target during the illusionary orbiting. According to one embodiment of my invention, the bob is a ballerina. The ballerina is similar in shape to an inverted cone and is a familiar and pleasant object for the observer. The ballerina is positioned so that one extended leg overlaps the conical fixation target. The colors of the overlapping areas are different to allow easy spacial recognition but similar enough to reduce visual clues of the actual planar movement of the bob during the observation of the stereo-illusion. In one embodiment the extended leg of the ballerina is black and overlaps a lilac portion of the cone and the skirt of the ballerina is lilac and overlaps the black tip of the cone.

As viewed through the eye pieces of my device, preferably illumination is provided in front of the ballerina. A Kodak grey card (25) of 18% reflectance serves as a suitable background for the ballerina (22). The ballerina moves in a pendulum motion in front of the cone (24) at a fixed rate of movement. Between the ballerina and the eye pieces (10) of my device is a reflective surface such as a mirror (35), angled so that when the ballerina and cone are illuminated, the images are viewed through eye pieces (10) located in the front of my device by reflection of the images off the reflective surface. The eye pieces contain clear lenses (11) and have rotating neutral filter wheels (13a, 13b) disposed behind them together with additional means for controlling the amount of light which is allowed to pass through each lens to the eye such as pivoting neutral density filters (14a, 15a, and 16a). My device contains means for digitally displaying the positions of the revolving filter wheels which relates to the luminance at the eye pieces.

According to a preferred embodiment of my invention, my device includes a printer (18) to record the digital display (17a, 17b) the moment the patient signals the visual endpoint during testing.

The neutral density filters are of two types—single value neutral density and circular variable neutral density filter wheels. Each single value filter is mounted on a pivot which allows rotation of the same filter before either eye. The single value filter can be superthreshold or subthreshold, that is above or below the density necessary to cause the stereo-illusion. Three single value neutral density filters of 0.1, 0.3, and 0.6 ND can be arranged in combinations varying the interocular neutral density difference from 0.1 to 0.9 ND in 0.1 ND increments. A circular variable neutral density filter wheel is mounted behind each eye piece and attenuates light linearly from zero to 2.0 ND. The two revolving filter wheels (13a, 13b) are connected by a shaft to electric motors (36a) and (36b) which are directly coupled to potentiometers (37a) and (37b) respectively. The electrical signals from the potentiometers are fed into computer (17) which processes the data and displays the position of the wheels in degrees from zero to 230 degrees. More particularly, my device can be readily understood and appreciated by reference to the drawings, FIGS. 1 to 7.

FIG. 5 is a section taken along lines 5/5 of FIG. 2 showing filter control knob 16 and single value neutral density 16a.

Figure 1:
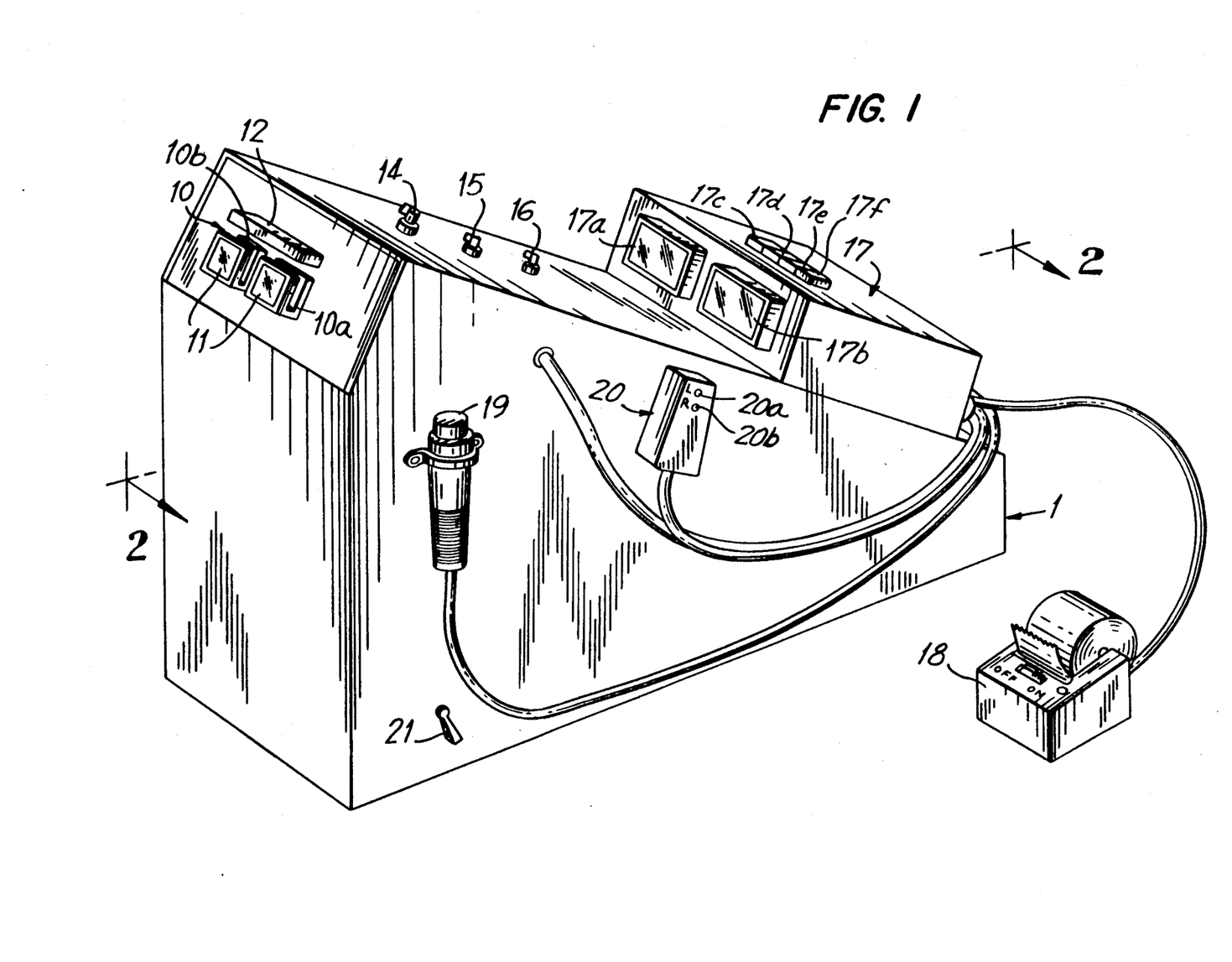
FIG. 1 is a front and side view of my device with the optional printer.

As can be seen from FIG. 1 my device comprises an enclosure 1 in which are disposed eye pieces 10, each of which has a clear lens 11, slots 10a and 10b for placing trial lenses, a forehead rest 12, and circular variable neutral density filter wheels 13a and 13b (best seen in FIG. 3) preferable 0.0 to 2.0 ND and powered by electric motors 36a and 36b. Behind filters 13a and 13b are pivot control knobs 14, 15, and 16 to rotate single value neutral density filters 14a, 15a, and 16a into the line of sight which are preferable 0.6, 0.3, and 0.1 ND respectively.

On the side of enclosure 1, I have shown switch 20 having left eye illumination control 20a and right eye illumination control 20b which forward, stop, and reverse the circular variable neutral density filter wheels 13a and 13b to adjust the level of brightness/dimness observed by each eye.

Computer 17 preferable has 5 controls, 17c, 17d, 17e, 17f and 19. Pressing control 17c initiates printer 18 to print the heading consisting of the words date, name, spontaneous C (standing for clockwise) and CC (standing for counter-clockwise) and evoked left and right. Control 17d initiates printing the word standard, control 17e initiates printing the word threshold, and 17f initiates printing the word neutralization. LED display 17a displays the position of filter wheel 13a in degrees, and 17b displays the position of filter wheel 13b. By pressing control 19 which is a trigger switch held by the patient the filter wheels stop revolving, the digital displays 17a and 17b are locked, and the printer prints the digits displayed under the appropriate heading previously selected by pressing control 17d, 17e, or 17f. On the rear panel of the computer is step-switch (34) that regulates the rotation speed of the filter wheels.

Figure 2:
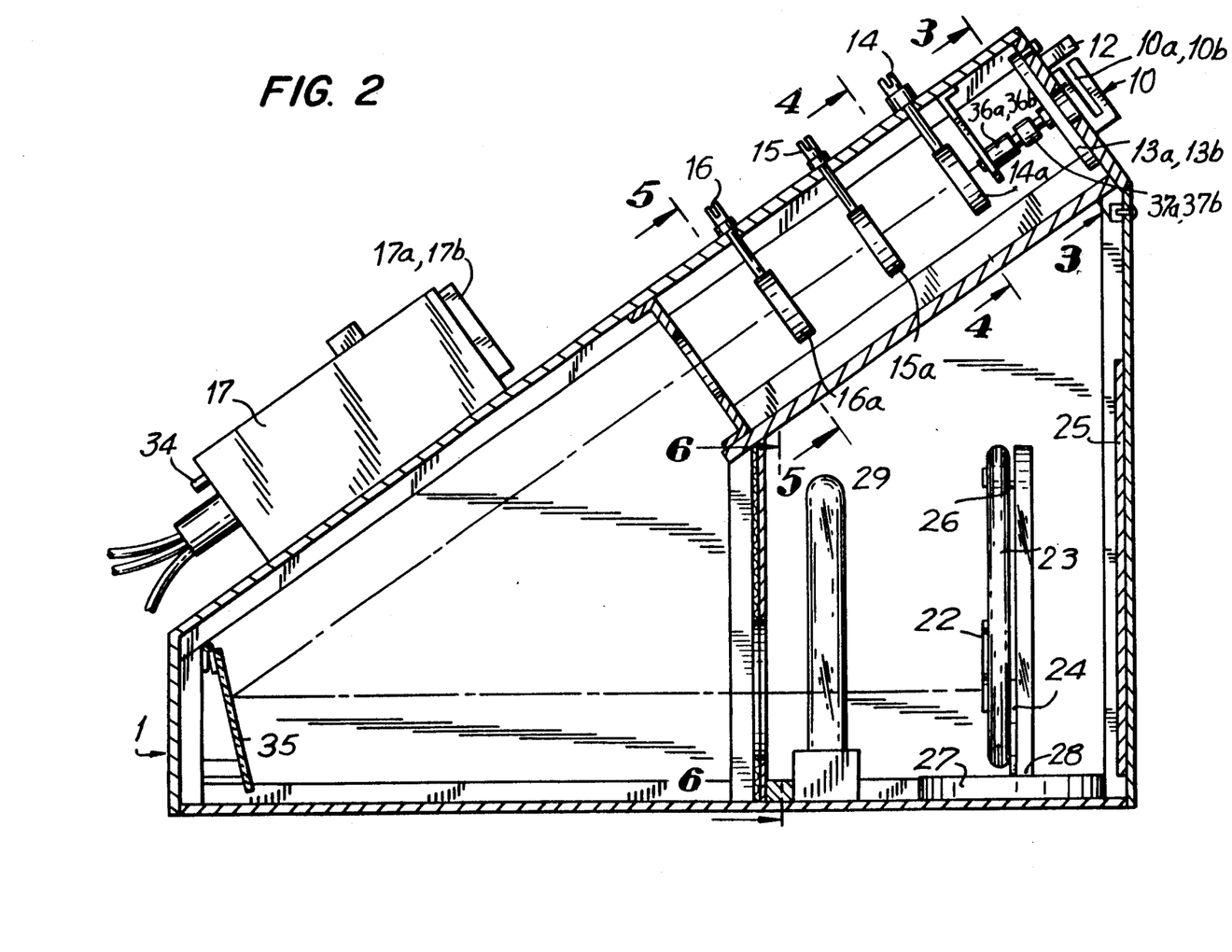
FIG. 2 is a sectional view taken along line 2/2 of FIG. 1.

As viewed through the clear lenses there is a sight line from the lenses to a reflective surface such as mirror 35 which reflects the image of the ballerina 22 and cone 24 to the viewer (see FIG. 2). According to the embodiment shown in FIGS. 1 and 2, the sight line from the clear lens to the reflective surface is from 12 to 60 inches. A convenient distance from the reflective surface to the ballerina is governed by the size of the enclosure. When, for example, the sight line is 52 inches, the distance from the reflective surface to the ballerina conveniently is about 22 inches. These distances can be varied with the size and construction of the device to optimize utilization or my device in a conveniently dimensioned enclosure.

Ballerina 22 is movable preferably by being secured to transparent plastic on ring 23 to enable the ballerina 22 to move in a pendulous manner. Ring 23 is driven by suitable motive means which is secured about pivot point 26. Means such as magnetic means 27, shown in FIG. 6 moves the pendulum in a short arc. Magnetic motive means have been found by me to be particularly useful but other functionally equivalent motive means can be used as well. The important aspect here is that the ballerina moves in a pendulum fashion at a constant rate.

Figure 6:
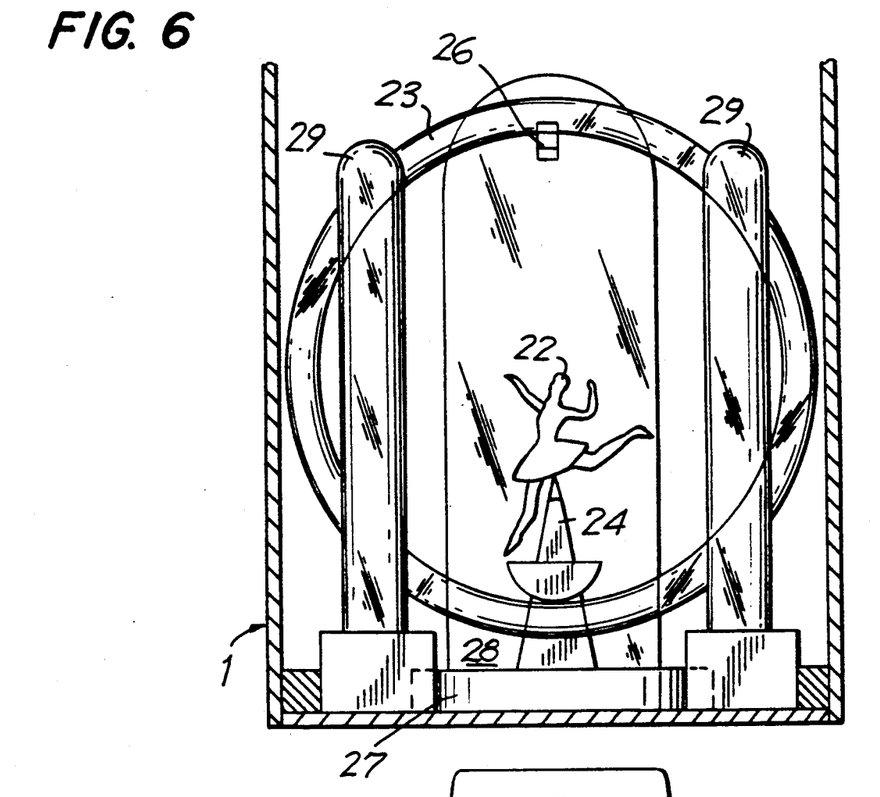
FIG. 6 is an enlarged view of the ballerina pendulum bob mounted on the transparent plastic ring positioned in front of the fixation cone and the semicircle plateform stage. The lights 29 are positioned in front of the bob and cone.
Figure 7:
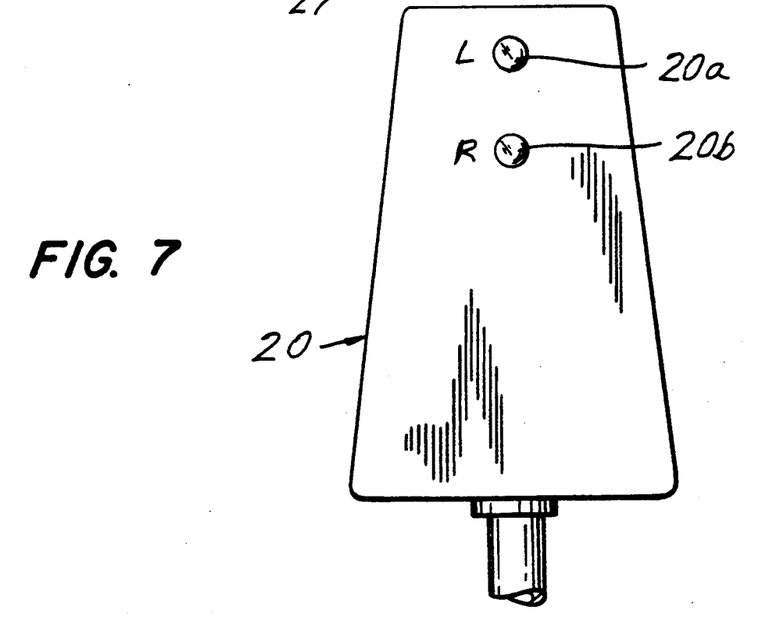
FIG. 7 shows control 20 which forwards, stops, and reverses the circular variable neutral density filter wheels 13a and 13b.

Cone 24 or other suitable reference point is affixed to a suitable transparent base 28 which may contain the motive or magnetic means 27. Suitable variable illumination sources are provided such as fluorescent light sources 29 are shown in FIGS. 2 and 6 for illuminating the ballerina and cone. These light sources are controlled by conventional electrical circuitry through switch 21 shown best in FIG. 1.

Figure 3:
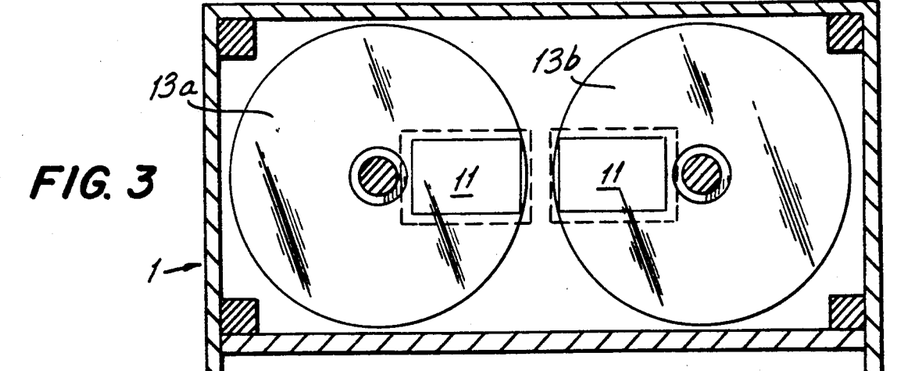
FIG. 3 is a section taken along the line 3/3 of FIG. 2 showing the circular variable neutral density filter wheels.
Figure 4:
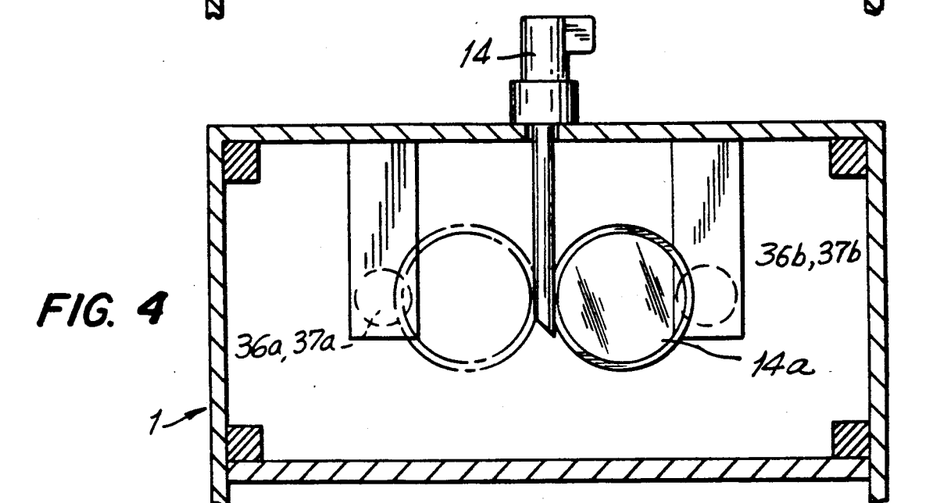
FIG. 4 is a section taken along lines 4/4 of FIG. 2 showing filter control knob 14, single value neutral density filter 14a, and electric motors 36a and 35b.
Figure 5:
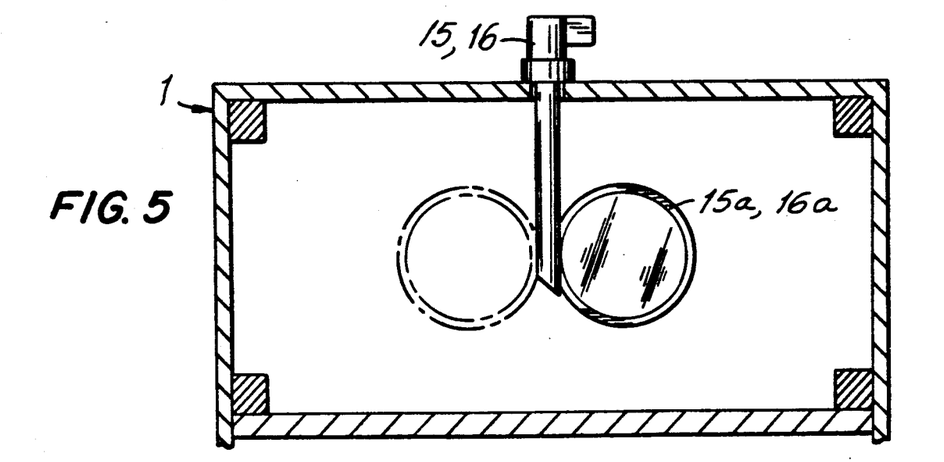

As best shown in FIG. 3 circular variable neutral density filter wheels 13a and 13b are disposed behind the clear lenses of +0.75 dioper power. FIG. 4 shows a 0.6 filter 14a controlled by knob 14 behind the filter wheels for placement in front of the left and right eye of the patient during testing. FIG. 5 shows a control 16 and the 0.1 ND filter 16a which may be rotated from one eye to another.

The use of my device of the present invention may be more readily appreciated by reference to one preferred embodiment shown in the drawing and by understanding what a person with normal vision will observe when that embodiment of my device is in operation. Without attenuating the light to either eye a normal-sighted person will observe the ballerina moving in a planar pendulous motion in front of the cone. When this observation has been established, the tester proceeds to the next step which involves an attempt to induce the physiologic (normal) stereo-illusion by diminishing light with a superthreshold single value neutral density filter by pivoting filter 14a into the line of sight of one eye to produce a sensation of the bob (ballerina) orbiting around the cone clockwise (filter over left eye) or counter-clockwise (filter over right eye). After it has been established that the subject appreciates the stereo-illusion with a super threshold filter the tester then pivots a subthreshold filter (16a) of 0.1 ND before either eye. If the subject experiences the stereo-illusion with the subthreshold filter before one and not the other eye, the eye covered by the filter during the sensation of the stereo-illusion has the brightness defect.

The quantitation of the threshold for the stereo-illusion induction and neutralization can be achieved by one of two methods. Methods #1 uses the neutral density filter wheels, and method #2 uses the pivoting fixed density neutral density filters. In method #1 the examiner places filters 14a, 15a, and 16a out of the line of sight and activates filter wheel 13a (left side) or 13b (right side) by moving switch 20a or 20b respectively to forward position. The subject indicates the moment when the stereo-illusion is seen (induction) by pressing the hand held switch 19 which stops the filter wheels and locks the digital display of the position of the filter wheels until the print-out by printer 18. The filter wheel is then reversed by placing switch 20a (left side) or 20b (right side) in the reverse position, and the subject is instructed to press switch 19 the moment the stereo-illusion ceases (neutralization), and these numbers are locked until printed. In method #2 the pivoting filters 14a, 15a, and 16a are positioned in various combinations to achieve the desired interocular neutral density difference varying from 0.1 to 0.9 ND in 0.1 increments. The endpoints for induction and neutralization are signalled by pressing switch 19, and the values are recorded by the examiner.

In order to see the stereo-illusion with this device, 20/60 or better acuity in each eye and stereopsis of at least 3000 seconds of arc are required. If, when either eye has been subjected to superthreshold light attenuation, the person being tested does not see the Pulfrich stereo-illusion phenomena of apparent rotation for the ballerina around the cone, this is indicative of diseases reducing visual acuity below 20/60 or stereopsis below 3000 seconds of arc.

The device of my invention is a useful diagnostic tool for detection of diseases which interfere with binocular vision. The testing procedure is simple and quick, as explained above. Children four years of age can reliably complete the test in two minutes. Since the test is simple, quick, and reliable, large populations can be readily screened for diseases which interfere with vision or impair optic nerve function. For example the test could be performed on all first grade students to detect disorders that would otherwise require formal ophthalmologic examination to include acuity, stereopsis, eye muscle coordination, visual evoked potention testing.

In addition to being useful as a screening test, my device is useful:
(1) To detect optic nerve involvement in patients suspect of having neurologic disease. The device would be used in the way the visual evoked potential test is used to measure optic nerve impairment.
(2) To quantitate visual or optic impairment by adjustable neutral density or polarizing filters in order to follow the progression or improvement of the disease process.
(3) To test for malingerer who claims vision loss. Other and further modifications of my device and uses will be more fully appreciated by those skilled in the visual and neurophysiologic sciences.

What is claimed is:
1. A device useful for measuring the Pulfrich stereo-illusion phenomenon in people with normal vision and without ocular and optic nerve disease and for diagnosing ocular and optic nerve diseases in people who are capable of experiencing the Pulfrich stereo-illusion phenomenon which comprises an enclosure having two eye pieces, a bob and a reference point for the bob wherein said bob is positioned below the top of the reference point but slightly in front of it when the patient to be tested is standing in front of the device, illumination means in front of the bob and reference point, reflective means for viewing the bob and reference point through the eye pieces, means for varying the amount of light perceived through the eye pieces by each of the eyes individually of the patient to be tested, means for varying the amount of illumination and means for causing the bob to arc in a pendulum movement in front of the reference point.

2. A device according to claim 1 wherein the means for causing the bob to arc comprises means which provide a smooth and regular pendulous motion of the bob.

3. A device according to claim 2 wherein said means includes means for causing said bob to appear to move, first in one direction and then when desired to stop and then move in the opposite direction.

4. A device according to claim 1 having left eye and right eye variable illumination means.

5. A device according to claim 1 having means for digitally recording desired points in the testing procedure.

6. A device according to claim 5 wherein the recordation means includes a printer.

7. A device according to claim 5 which comprises display means.

8. A device according to claim 1 wherein the bob is a ballerina.

9. A device according to claim 8 wherein the ballerina is secured to a pendulum.

10. a device according to claim 9 wherein the pendulum is moved by magnetic means in the desired arc.

11. a device according to claim 1 wherein the bob is an inverted conical structure having a ballerina with a dress of lighter color than the ballerina figure secured to a pendulum.

12. A device according to claim 1 wherein the reference point is a cone.

13. A method of measuring the Pulfrich stereo-illusion phenomenon in people with normal vision and without ocular and optic nerve disease and for diagnosing ocular and optic nerve disease in people who are capable of experiencing the Pulfrich stereo-illusion phenomenon which comprises positioning a person to be tested at the eye pieces of a device which comprises an enclosure having two eye pieces, a bob and a reference point for the bob where said bob is positioned below the top of the reference point but slightly in front of it when the patient to be tested is standing in front of the device, illumination means in front of the bob and reference point, reflective means for viewing the bob and reference point through the eye pieces, means for varying the amount of light perceived through the eye pieces by each of the eyes individually of the patient to be tested, means for varying the amount of the patient to be tested, means for varying the amount of illumination and means for causing the bob to arc in a pendulum movement in front of the reference point, illuminating the bob, reference point, and background within the enclosure, activating the bob, determining if the person sees the bob traversing in front of the reference point in a planar path with both eyes with full vision, diminishing the amount of light received by one eye, determining how the person sees the bob in relation to the reference point as the amount of light received by one eye is varied, restoring full vision to the first eye, diminishing the amount of light received by the other eye in the same manner, determining how the person sees the bob in relation to the reference point with the other eye, and repeating the above steps using the means for varying the amount of light perceived and recording the endpoints of induction and neutralization of the stereo-illusion.

14. A method of measuring the Pulfrich stereo-illusion phenomenon in people with normal vision and without ocular and optic nerve disease and for diagnosing ocular and optic diseases in people who are capable of experiencing the Pulfrich stereo-illusion phenomenon which comprises positioning a person to be tested at the eye pieces of a device which comprises an enclosure having two eye pieces, a bob and a reference point for the bob wherein said bob is positioned below the top of the reference point but slightly in front of it when the patient to be tested is standing in front of the device, illumination means in front of the bob and reference point, reflective means for viewing the bob and reference point through the eye pieces, means for varying the amount of light perceived through the eye pieces by each of the eyes individually of the patient to be tested, means for varying the amount of illumination and means for causing the bob to arc in a pendulum movement in front of the reference point which comprises means which provide a smooth and regular pendulous motion of the bob, illuminating the bob, reference point, and background within the enclosure, activating the bob, determining if the person sees the bob traversing in front of the reference point in a planar path with both eyes with full vision, diminishing the amount of light received by one eye, determining how the person sees the bob in relation to the reference point as the amount of light received by one eye is varied, restoring full vision to the first eye, diminishing the amount of light received by the other eye in the same manner, determining how the person sees the bob in relation to the reference point with the other eye, and repeating the above steps using the means for varying the amount of light perceived and recording the endpoints of induction and neutralization of the stereo-illusion.

15. A method of measuring the Pulfrich stereo-illusion phenomenon in people with normal vision and without ocular and optic nerve disease and for diagnosing ocular and optic diseases in people who are capable of experiencing the Pulfrich stereo-illusion phenomenon which comprises positioning a person to be tested at the eye pieces of a device which comprises an enclosure having two eye pieces, a bob and a reference point for the bob wherein said bob is positioned below the top of the reference point but slightly in front of it when the patient to be tested is standing in front of the device, illumination means in front of the bob and reference point, reflective means for viewing the bob and reference point through the eye pieces, means for varying the amount of light perceived through the eye pieces by each of the eyes individually of the patient to be tested, means for varying the amount of illumination and means for causing the bob to arc in a pendulum movement in front of the reference point which comprises means which provide a smooth and regular pendulous motion of the bob, which means includes means for causing said bob to appear to move, first in one direction and then when desired to stop and then move in the opposite direction, illuminating the bob, reference point, and background within the enclosure, activating the bob, determining if the person sees the bob traversing in front of the reference point in a planar path with both eyes with full vision, diminishing the amount of light received by one eye, determining how the person sees the bob in relation to the reference point as the amount of light received by one eye in varied, restoring full vision to the first eye, diminishing the amount of light received by the other eye in the same manner, determining how the person sees the bob in relation to the reference point with the other eye, and repeating the above steps using the means for varying the amount of light perceived and recording the endpoints of induction and neutralization of the stereo-illusion.

16. A method of measuring the Pulfrich stereo-illusion phenomenon in people with normal vision and without ocular and optic nerve disease and for diagnosing ocular and optic diseases in people who are capable of experiencing the Pulfrich stereo-illusion phenomenon which comprises positioning a person to be tested at the eye pieces of a device which comprises an enclosure having two eye pieces, a bob and a reference point for the bob wherein said bob is positioned below the top of the reference point but slightly in front of it when the patient to be tested is standing in front of the device, left eye and right eye variable illumination means in front of the bob and reference point, reflective means for viewing the bob and reference point through the eye pieces, means for varying the amount of light perceived through the eye pieces by each of the eyes individually of the patient to be tested, means for varying the amount of illumination and means for causing the bob to arc in a pendulum movement in front of the reference point, illuminating the bob, reference point, and background within the enclosure, activating the bob, determining if the person sees the bob traversing in front of the reference point in a planar path with both eyes with full vision, diminishing the amount of light received by one eye, determining how the person sees the bob in relation to the reference point as the amount of light received by one eye is varied, restoring full vision to the first eye, diminishing the amount of light received by the other eye in the same manner, determining how the person sees the bob in relation to the reference point with the other eye, and repeating the above steps using the means for varying the amount of light perceived and recording the endpoints of induction and neutralization of the stereo-illusion.

17. A method of measuring the Pulfrich stereo-illusion phenomenon in people with normal vision and without ocular and optic nerve disease and for diagnosing ocular and optic diseases in people who are capable of experiencing the Pulfrich stereo-illusion which comprises positioning a person to be tested at the eye pieces of a device which comprises an enclosure having two eye pieces, a bob and a reference point for the bob wherein said bob is positioned below the top of the reference point but slightly in front of it when the patient to be tested is standing in front of the device, illumination means in front of the bob and reference point, reflective means for viewing the bob and reference point through the eye pieces, means for varying the amount of light perceived through the eye pieces by each of the eyes individually of the patient to be tested, means for varying the amount of illumination, means for causing the bob to arc in a pendulum movement in front of the reference point and means for digitally recording desired points in the testing procedure, illuminating the bob, reference point, and background within the enclosure, activating the bob, determining if the person sees the bob traversing in front of the reference point in a planar path with both eyes with full vision, diminishing the amount of light received by one eye, determining how the person sees the bob in relation to the reference point as the amount of light received by one eye is varied, restoring full vision to the first eye, diminishing the amount of light received by the other eye in the same manner, determining how the person sees the bob in relation to the reference point with the other eye, and repeating the above steps using the means for varying the amount of light perceived and recording the endpoints of induction and neutralization of the stereo-illusion and digitally recording desired points in the testing procedure.

18. A method of measuring the Pulfrich stereo-illusion phenomenon in people with normal vision and without ocular and optic nerve disease and for diagnosing ocular and optic diseases in people who are capable of experiencing the Pulfrich stereo-illusion phenomenon which comprises positioning a person to be tested at the eye pieces of a device which comprises and enclosure having two eye pieces, a bob and a reference point for the bob wherein said bob is positioned below the top of the reference point but slightly in front of it when the patient to be tested is standing in front of the device, illumination means in front of the bob and reference point, reflective means for viewing the bob and reference point through the eye pieces, means for varying the amount of light perceived through the eye pieces by each of the eyes individually of the patient to be tested, means for varying the amount of illumination, means for causing the bob to arc in a pendulum movement in front of the reference point and means for digitally recording desired points in the testing procedure and for printing desired data, illuminating the bob, reference point, and background within the enclosure, activating the bob, determining if the person sees the bob traversing in front of the reference point in a planar path with both eyes with full vision, diminishing the amount of light received by one eye, determining how the person sees the bob in relation to the reference point as the amount of light received by one eye is varied, restoring full vision to the first eye, diminishing the amount of light received by the other eye in the same manner, determining how the person sees the bob in relation to the reference point with the other eye, and repeating the above steps using the means for varying the amount of light perceived and recording the endpoints of induction and neutralization of the stereo-illusion and digitally recording desired points in the testing procedure.

19. A method of measuring the Pulfrich stereo-illusion phenomenon in people with normal vision and without ocular and optic nerve disease and for diagnosing ocular and optic diseases in people who are capable of experiencing the Pulfrich stereo-illusion phenomenon which comprises positioning a person to be tested at the eye pieces of a device which comprises an enclosure having two eye pieces, a bob and a reference point for the bob wherein said bob is positioned below the top of the reference point but slightly in front of it when the patient to be tested is standing in front of the device, illumination means in front of the bob and reference point, reflective means for viewing the bob and reference point through the eye pieces, means for varying the amount of light perceived through the eye pieces by each of the eyes individually of the patient to be tested, means for varying the amount off illumination, means for causing the bob to arc in a pendulum movement in front of the reference point and means for digitally recording and visually displaying desired points in the testing procedure, illuminating the bob, reference point, and background within the enclosure, activating the bob, determining if the person sees the bob traversing in front of the reference point in a planar path with both eyes with full vision, diminishing the amount of light received by one eye, determining how the person sees the bob in relation to the reference point as the amount of light received by one eye is varied, restoring full vision to the first eye, diminishing the amount of light received by the other eye in the same manner, determining how the person sees the bob in relation to the reference point with the other eye, and repeating the above steps using the means for varying the amount of light perceived and recording the endpoints of induction and neutralization of the stereo-illusion.

20. A method of measuring the Pulfrich stereo-illusion phenomenon in people with normal vision and without ocular and optic nerve disease and for diagnosing ocular and optic diseases in people who are capable of experiencing the Pulfrich stereo-illusion phenomenon which comprises positioning a person to be tested at the eye pieces of a device which comprises an enclosure having two eye pieces, a bob comprising a ballerina and a reference point for the ballerina wherein said ballerina is positioned below the top of the reference point but slightly in front of it when the patient to be tested is standing in front of the device, illumination means in front of the ballerina and reference point, reflective means for viewing the ballerina and reference point through the eye pieces, means for varying the amount of light perceived through the eye pieces by each of the eyes individually of the patient to be tested, means for varying the amount of illumination and means for causing the ballerina to arc in a pendulum movement in front of the reference point, illuminating the ballerina, reference point and background within the enclosure, activating the ballerina, determining if the person sees the ballerina traversing in front of the reference point with both eyes with full vision, diminishing the amount of light received by one eye, determining how the person sees the ballerina in relation to the reference point as the amount of light received by one eye is varied, restoring full vision to the first eye, diminishing the amount of light received by the other eye in the same manner and determining how the person sees the ballerina in relation to the reference point with the other eye, and repeating the above steps using the means for varying the amount of light perceived and recording the endpoints of induction and neutralization of the stereo-illusion.

21. A method of measuring the Pulfrich stereo-illusion phenomenon in people with normal vision and without ocular and optic nerve disease and for diagnosing ocular and optic diseases in people who are capable of experiencing the Pulfrich stereo-illusion phenomenon which comprises positioning a person to be tested at the eye pieces of a device which comprises an enclosure having two eye pieces, a bob comprising a ballerina secured to a pendulum and a reference point for the ballerina wherein said ballerina is positioned below the top of the reference point but slightly in front of it when the patient to be tested is standing in front of the device, illumination means in front of the ballerina and reference point, reflective means for viewing the ballerina and reference point through the eye pieces, means for varying the amount of light perceived through the eye pieces by each of the eyes individually of the patient to be tested, means for varying the amount of illumination and means for causing the ballerina to arc in a pendulum movement in front of the reference point, illuminating the ballerina, reference point and background within the enclosure, activating the ballerina, determining if the person sees the ballerina traversing in front of the reference point with both eyes with full vision, diminishing the amount of light received by one eye, determining how the person sees the ballerina in relation to the reference point as the amount of light received by one eye is varied, restoring full vision to the first eye, diminishing the amount of light received by the other eye in the same manner and determining how the person sees the ballerina in relation to the reference point with the other eye, and repeating the above steps using the means for varying the amount of light perceived and recording the endpoints of induction and neutralization of the stereo-illusion.

22. A method of measuring the Pulfrich stereo-illusion phenomenon in people with normal vision and without ocular and optic nerve disease and for diagnosing ocular and optic diseases in people who are capable of experiencing the Pulfrich stereo-illusion phenomenon which comprises positioning a person to be tested at the eye pieces of a device which comprises an enclosure having two eye pieces, a bob comprising a ballerina secured to a pendulum and a reference point for the ballerina wherein said ballerina is positioned below the top of the reference point but slightly in front of it when the patient to be tested is standing in front of the device, illumination means in front of the ballerina and reference point, reflective means for viewing the ballerina and reference point through the eye pieces, means for varying the amount of light perceived through the eye pieces by each of the eyes individually of the patient to be tested, means for varying the amount of illumination and magnetic means for causing the ballerina to arc in a pendulum movement in front of the reference point, illuminating the ballerina, reference point and background within the enclosure, activating the ballerina, determining if the person sees the ballerina traversing in front of the reference point with both eyes with full vision, diminishing the amount of light received by one eye, determining how the person sees the ballerina in relation to the reference point as the amount of light received by one eye is varied, restoring full vision to the first eye, diminishing the amount of light received by the other eye in the same manner and determining how the person sees the ballerina in relation to the reference point with the other eye, and repeating the above steps using the means or varying the amount of light perceived and recording the endpoints of induction and neutralization of the stereo-illusion.

23. A method of measuring the Pulfrich stereo-illusion phenomenon in people with normal vision and without ocular and optic nerve disease and for diagnosing ocular and optic diseases in people who are capable of experiencing the Pulfrich stereo-illusion phenomenon which comprises positioning a person to be tested at the eye pieces of a device which compromises and enclosure having two eye pieces, a bob comprising an inverted conical structure having a ballerina with a dress of lighter color than the ballerina figure secured to a pendulum and a reference point for the ballerina wherein said ballerina is positioned below the top of the reference point but slightly in front of it when the patient to be tested is standing in front of the device, illumination means in front of the ballerina and reference point, reflective means for viewing the ballerina and reference point through the eye pieces, means for varying the amount of light perceived through the eye pieces by each of the eyes individually of the patient to be tested, means for varying the amount of illumination and means for causing the ballerina to arc in a pendulum movement in front of the reference point, illuminating the ballerina, reference point and background within the enclosure, activating the ballerina, determining if the person sees the ballerina traversing in front of the reference point with both eyes with full vision, diminishing the amount of light received by one eye, determining how the person sees the ballerina in relation to the reference point as the amount of light received by one eye is varied, restoring full vision to the first eye, diminishing the amount of light received by the other eye in the same manner and determining how the person sees the ballerina in relation to the reference point with the other eye, and repeating the above steps using the means for varying the amount of light perceived and recording the endpoints of induction and neutralization of the stereo-illusion.

24. A method of measuring the Pulfrich stereo-illusion phenomenon in people with normal vision and without ocular and optic nerve disease and for diagnosing ocular and optic diseases in people who are capable of experiencing the Pulfrich stereo-illusion phenomenon which comprises positioning a person to be tested at the eye pieces of a device which comprises and enclosure having two eye pieces, a bob and a reference point for the bob comprising a cone wherein said bob is positioned below the point of the cone, reflective means for viewing the bob and the cone through the eye pieces, means for varying the amount of light perceived through the eye pieces by each of the eyes individually of the patient to be tested, means for varying the amount of illumination and means for causing the bob to arc in a pendulum movement in front of the cone, illuminating the bob, cone and background, activating the bob, determining if the person sees the objects traversing in front of the cone in a planer path with both eyes with full vision, diminishing the amount of light received by the one eye, determining how the person sees the bob in relation to the cone as the amount of light received by one eye is varied, restoring full vision to the first eye, diminishing the amount of light received by the other eye in the same manner, determining how the person sees the bob in relation to the cone with the other eye, and repeating the above steps using the means for varying the amount of light perceived and recording the endpoints of induction and neutralization of the stereo-illusion.

* * * * *

UNITED STATES PATENT AND TRADEMARK OFFICE
CERTIFICATE OF CORRECTION

PATENT NO. : 5,099,858

DATED : March 31, 1992

INVENTOR(S) : Albert J. Hofeldt

It is certified that error appears in the above-identified patent and that said Letters Patent is hereby corrected as shown below:

Column 7, line 53, delete in its entirety; and line 54, delete "tested".

Signed and Sealed this

Fifteenth Day of August, 1995

Attest:

BRUCE LEHMAN

Attesting Officer    Commissioner of Patents and Trademarks